United States Patent [19]
Gutcho et al.

[11] 4,105,410
[45] Aug. 8, 1978

[54] RECEPTOR COATED PLASTIC FOR ASSAY OF LIGANDS

[75] Inventors: Sidney Gutcho, Monsey; Henry McCarter, Pine Island; Edward Chanod, Staten Island, all of N.Y.

[73] Assignee: Becton, Dickinson and Company, Rutherford, N.J.

[21] Appl. No.: 707,683

[22] Filed: Jul. 22, 1976

[51] Int. Cl.$^2$ .................... G01N 29/02; G01N 31/00; A61K 29/00
[52] U.S. Cl. ................. 23/253 TP; 424/12; 252/408; 427/2
[58] Field of Search .......... 427/2; 23/253 TP, 230 B; 424/12; 252/408

[56] References Cited
U.S. PATENT DOCUMENTS

| 3,646,346 | 2/1972 | Catt ................................ 424/12 |
| 3,690,834 | 9/1972 | Goldstein ................ 23/230 B X |

*Primary Examiner*—Ronald H. Smith
*Assistant Examiner*—Sam Silverberg
*Attorney, Agent, or Firm*—Marn & Jangarathis

[57] ABSTRACT

A receptor is coated on a plastic substrate, such as a tube, from a solution containing a blocking agent for the receptor sites to prevent adherence of the receptor sites to the plastic substrate, and a deaggregating agent for the receptor to prevent adherence in dimers or aggregates which block receptor sites, thereby reducing receptor requirements.

12 Claims, No Drawings

RECEPTOR COATED PLASTIC FOR ASSAY OF LIGANDS

This invention relates to assay of ligands, and more particularly, to an improved process for providing a receptor coated on a plastic substrate suitable for the assay of ligands and the product thereof.

The assay of ligands is based on the competition between a labeled and unlabeled ligand for a limited number of sites on a receptor for the ligand. In brief, a known quantity of labeled ligand, a sample containing an unknown quantity of unlabeled ligand and a known quantity of receptor for the ligand are combined, and the percentage of labeled ligand bound to the receptor will depend upon the quantity of unlabeled ligand in the sample. After the receptor, including bound ligand, is separated from the sample the amount of labeled ligand bound to the receptor or remaining in the sample is determined and compared with a standard curve to determine the quantity of unlabeled ligand which was present in the sample.

In order to facilitate separation of the receptor from the sample, in many cases, the receptor is bound to a plastic substrate such as a tube whereby the receptor including bound ligand can be easily separated from a sample for making the determination as to the quantity of labeled ligand which is either bound to the receptor or remains free in the sample.

The present invention is directed to providing improvements in the production of a receptor coated on a plastic substrate for the assay of a ligand.

In accordance with the present invention, a receptor is coated on a plastic substrate in the presence of a deaggregation agent for the receptor and a blocking agent for the ligand receptor sites in order to effect adherence of the receptor to the plastic substrate at other than the receptor sites.

More particularly, the blocking agent is a substance which has a limited cross-reactivity with the receptor in order to effect blocking of the ligand receptor sites to thereby prevent adherence of the receptor to the plastic at the ligand receptor sites, while also permitting subsequent binding of a ligand to the receptor. In general, the substance employed as a blocking agent for the ligand receptor sites has a cross-reactivity with the receptor of from about 0.0001 to about 5%, and preferably from about 0.001 to about 1%. The upper limit of the cross-reactivity insures that in a subsequent assay the blocking agent can be displaced by the ligand to be assayed whereby there can be competitive binding at the receptor sites. As should be apparent, the substance employed as a blocking agent should have an affinity for the plastic surface which is lower than the affinity of the receptor for the plastic surface in order to permit orientation of the receptor on the plastic. The substance employed as a blocking agent is preferably hydrophilic; however, it is to be understood that non-hydrophilic substances can also be employed.

As representative examples of suitable blocking agents, there may be mentioned; cardiac glycosides, such as, ouabain, gitoxin, gitaloxin, acetyl strophanthidin, etc.; steroids, such as, progesterone, testosterone, cortisol, etc.

The selection of a suitable agent for blocking the receptor sites is deemed to be within the scope of those skilled in the art from the teachings herein.

The coating of antibody on the plastic substrate is also effected in the presence of a deaggregating agent for the receptor in order to maintain monomeric antibody and to prevent adherence to the plastic substrate in dimers or aggregates, which would limit the availability of receptor sites in the subsequent assay. The deaggregating agent may be one of a wide variety of such agents which are used in the art, and as representative examples of such agents, there may be mentioned: amino acids, such as, glycine, lysine, etc.; urea; guanidine; soluble inorganic salts; in particular, sodium and calcium salts, and the like. The selection of a suitable deaggregating agent is deemed to be within the scope of those skilled in the art from the teachings herein.

The blocking agent is employed in an amount effective for blocking the receptor sites of the receptor for the ligand, which will vary with the amount of receptor and the particular receptor employed. In general, the blocking agent is employed in an amount of from 0.0001 to 0.1%, preferably from 0.0005 to 0.005%, all weight percent of solution. Similarly, the amount of deaggregating agent employed is dependent on the receptor and amount thereof, with the deaggregating agent generally being employed in an amount of from 0.01M to 0.9M, preferably from 0.25M to 0.35M. The amount of blocking agent and deaggregating agent to be employed is deemed to be within the scope of those skilled in the art from the teachings herein.

It has been found that by coating the plastic substrate with antibody in the presence of both a blocking agent and a deaggregating agent, the amount of receptor required for the coating is significantly lower than that required in prior art techniques.

The plastic substrate is coated with the receptor at temperatures generally employed in the art; e.g., temperatures in the order of 50° F to 100° F, and for a time sufficient to insure adherence of the receptor to the plastic substrate; e.g., time in the order of 15 minutes to 24 hours. The antibody coated tube is generally further treated with a protein containing buffer in order to coat any uncoated portions and reduce or eliminate non-specific binding in a subsequent assay. After drying of the plastic substrate, the receptor coated plastic substrate, may be employed for an assay by procedures known in the art.

The receptor coated on the plastic substrate may be either an elicited antibody or a naturally occuring receptor and such receptors are well known in the art. As known in the art, the antibodies are elicited by injection of an antigen or a hapten bound to an antigenic carrier into the blood stream of a vertebrate, with such antibody being a specific receptor for such antigen or hapten.

The receptor coated plastic substrate may be employed for the assay of a wide variety of ligands, such as (1) antigens, which when introduced into the blood stream of a vertebrate, result in the formation of antibodies; (2) haptens, which when bound to an antigenic carrier and introduced into the blood stream of a vertebrate, produce antibodies specific for the hapten, or (3) ligands which have naturally occuring receptors which can be isolated in a form specific for the ligand. It is to be understood that a ligand can have naturally occuring receptors and also function as a hapten when bound to a protein.

As representative examples of ligands to which the present invention is applicable, there may be mentioned: polypeptides, nucleotides, nucleosides and proteins, such as ACTH, oxytocin, luteinizing hormone, insulin, proinsulin, Bence-Jones protein, charionic gonadotropin, pituitary gonadotropin, growth hormone, renin, thyroxine binding globulin, bradykinin, angiotensin, follicle stimulating hormone; cyclic AMP, cholylglycine, cyclic GMP, etc,; steroids, including: estrogens, gestrogens, androgens, adrenocortical hormones, bile acids, cardiotonic glycosides, aglycones as well as saponins. As specific examples, these may be mentioned: thyroxine, triiodothyronine, testosterone, adrosterone, estrone, estriol, progesterone, pregnenolene, 17-hydroxydeoxycorticosterone (compound S), deoxycorticoserone, cortisone, corticosterone, cortisol, aldosterone, digoxin, digitoxin; etc., vitamins, such as vitamin A, the B vitamin group, vitamin C, the D vitamins, folic acid and vitamins E and K; and miscellaneous ligands, such as antigens for viral hepatitis A and B, Rubella, Herpes Simplex, α-feto protein, etc.

The above substances are only representative, and it is understood that such substances can be used as appropriate analogs.

The assay employing the receptor coated plastic substrate may be effected by the use of a labeled ligand; e.g., labeled with a radioisotope, enzyme, fluorescent substance, etc. Such procedures are known in the art and form no part of the present invention and, accordingly, no further details in this respect are required for an understanding of the invention.

The plastic or polymeric substrate may be in particulate form, in the form of a tube, sheet form, etc., with a tube being preferred. The plastic may be any one of a wide variety of polymers generally employed as substrates for a receptor, including, for example, polystyrene, polyethylene, polypropylene, polyamides, polyacrylamides, etc. The choice of a particular plastic substrate should be apparent to those skilled in the art from the teachings herein.

The invention will be further described with respect to the following examples; however, the scope of the invention is not to be limited thereby.

EXAMPLE I

Digoxin antibody, elicited in sheep with a digoxin-human serum albumin conjugate, in an aqueous buffer solution [0.05M carbonate/bicarbonate, pH 9.6, 0.3M glycine, 0.001% ouabain and 0.005% chloramphenicol] is added (1.0 ml) to a polystyrene tube, at room temperature and maintained at room temperature for 1 hour, followed by aspiration of the fluid from the tube. A buffer solution (0.1M phosphate, pH 7.0, with 0.9% NaCl and 0.1% NaN$_3$), including 1 g of lysozyme per liter, is added to the tube and held at room temperature for about 15 minutes. The fluid is aspirated from the tube, and the tubes dried in vacuo at ambient temperature.

EXAMPLE II

The antibody coated tubes, prepared as in Example I are used for digoxin assay as follows:

1. At room temperature, 50 μl of Digoxin standard or Patient sample, 100 μl of 3-0-succinyl digoxigenin tyrosine ($^{125}$I) NS 1000 μl of 0.1M phosphate buffered saline (PBS) are pipetted into the tubes as follows:

| Tube No. | Digoxin in Standard (ng/ml) |
|---|---|
| 1,2 | 0.0 |
| 3,4 | 0.5 |
| 5,6 | 1.0 |

-continued

| Tube No. | Digoxin in Standard (ng/ml) |
|---|---|
| 7,8 | 1.5 |
| 9,10 | 2.0 |
| 11, 12 | 3.0 |
| 13, 14 | 5.0 |
| 15, 16 etc. | Patient Samples |

The tubes are incubated in a water bath at 37° C for 60 minutes.

2. The liquor is aspirated from the tubes, followed by addition of 1.0 - 1.5 ml PBS and aspiration (decanting). The tubes now contain labeled and unlabeled digoxin bound to antibody.

3. The tubes are counted in sequence for at least 0.5 minute with a gamma-counter and a standard curve is prepared which covers the range of 0.5 - 5.0 ng digoxin per ml of patient sample.

4. The digoxin concentration in the sample is obtained from the standard curve.

The present invention is particularly advantageous in that high titers of receptor can be employed for coating the plastic substrate; e.g., the antibody concentration can be one-tenth to one-fifth of previous antibody concentrations, a 5-fold to 10-fold increase in antibody titer.

Numerous modifications and variations of the present invention are possible in light of the above teachings and, therefore, within the scope of the appended claims, the invention may be practiced otherwise than as particularly described.

What is claimed is:

1. In a process for coating a receptor for a ligand to be assayed on a plastic substrate, the improvement comprising:
    effecting said coating with a solution of the receptor containing a blocking agent for the receptor sites to prevent adherence of the receptor sites to the plastic substrate and a deaggregating agent for the receptor to prevent adherence of the receptor to the plastic substrate in aggregates, said blocking agent having a cross-reactivity with the receptor of from 0.0001 to 5% and which can be displaced by the ligand to be assayed.

2. The process of claim 1 wherein the blocking agent is employed in an amount of from 0.001 to 0.01%, by weight, of the solution.

3. The process of claim 2 wherein the deaggregating agent is employed in a concentration of from 0.01M to 0.9M.

4. The process of claim 3 wherein the blocking agent is selected from the group consisting of cardiac glycosides and steroids.

5. The process of claim 4 wherein the plastic substrate is in the form of a tube.

6. The process of claim 5 wherein the plastic is polystyrene.

7. The process of claim 6 wherein the receptor is a digoxin antibody.

8. The process of claim 7 wherein the blocking agent is ouabain.

9. The process of claim 8 wherein the deaggregating agent is glycine.

10. The process of claim 1 and further comprising treating the receptor coated plastic with a protein containing buffer to coat any uncoated portions of the plastic substrate with protein.

11. A plastic substrate having a receptor for a ligand coated thereon produced by the process of claim 1.

12. The process of claim 1 wherein the blocking agent has a cross-reactivity of from 0.001 to 1%.

* * * * *